(12) United States Patent
Colonna

(10) Patent No.: US 9,918,868 B2
(45) Date of Patent: Mar. 20, 2018

(54) BODILY SUPPORT ASSEMBLY

(71) Applicant: Richard Colonna, Pittsburgh, PA (US)

(72) Inventor: Richard Colonna, Pittsburgh, PA (US)

(*) Notice: Subject to any disclaimer, the term of this patent is extended or adjusted under 35 U.S.C. 154(b) by 300 days.

(21) Appl. No.: 14/687,283

(22) Filed: Apr. 15, 2015

(65) Prior Publication Data

US 2016/0302958 A1    Oct. 20, 2016

(51) Int. Cl.
*A61F 5/37*    (2006.01)

(52) U.S. Cl.
CPC ................. *A61F 5/3738* (2013.01)

(58) Field of Classification Search
CPC .......... A61F 5/00; A61F 5/0118; A61F 5/013; A61F 5/37; A61F 5/3723; A61F 5/373; A61F 5/3738; A61F 5/3746; A61F 5/058; A61F 5/05841; A61F 5/05858; A47G 9/06; A47G 9/066; A41D 13/05; A41D 13/08
USPC ........ 602/4, 20, 21; 128/869, 875, 876, 878; 2/16
See application file for complete search history.

(56) References Cited

U.S. PATENT DOCUMENTS

| 2,560,243 | A |   | 7/1951  | Peterson |
|-----------|---|---|---------|----------|
| D273,516  | S | * | 4/1984  | Saal ................................ 602/20 |
| 4,526,164 | A | * | 7/1985  | Bihl ..................... A61F 5/3738 602/4 |
| 4,877,038 | A | * | 10/1989 | Fricke ................... A61F 5/3784 128/869 |
| 5,086,762 | A |   | 2/1992  | Chee |
| 6,190,340 | B1|   | 2/2001  | Borell |
| 6,435,185 | B1|   | 8/2002  | Schimpf |
| 6,643,870 | B2|   | 11/2003 | Bertrand |
| 6,966,069 | B2|   | 11/2005 | Booth |
| D571,475  | S |   | 6/2008  | Estep |
| 8,197,429 | B2|   | 1/2012  | Neseem |
| 2003/0226187 | A1 | * | 12/2003 | Arana .................... A61F 5/3738 2/16 |
| 2007/0208286 | A1 | * | 9/2007 | Brooks ................. A61F 5/3738 602/4 |
| 2015/0216712 | A1 | * | 8/2015 | Wilson, Jr. ........... A61F 5/3738 602/4 |

\* cited by examiner

*Primary Examiner* — Tarla Patel

(57) ABSTRACT

A bodily support assembly includes a bag that may insertably receive each of pair of forearms of a user. A first strap is attached to the bag and a first coupler is attached to the first strap. A second strap is attached to the bag and the second strap may be extended around a neck of a user. A second coupler is attached to the second strap and the second coupler is complementary with respect to the first coupler. Thus, the first coupler and the second coupler retain the first strap and the second strap around the user's neck thereby facilitating the bag to support the user's forearms.

5 Claims, 3 Drawing Sheets

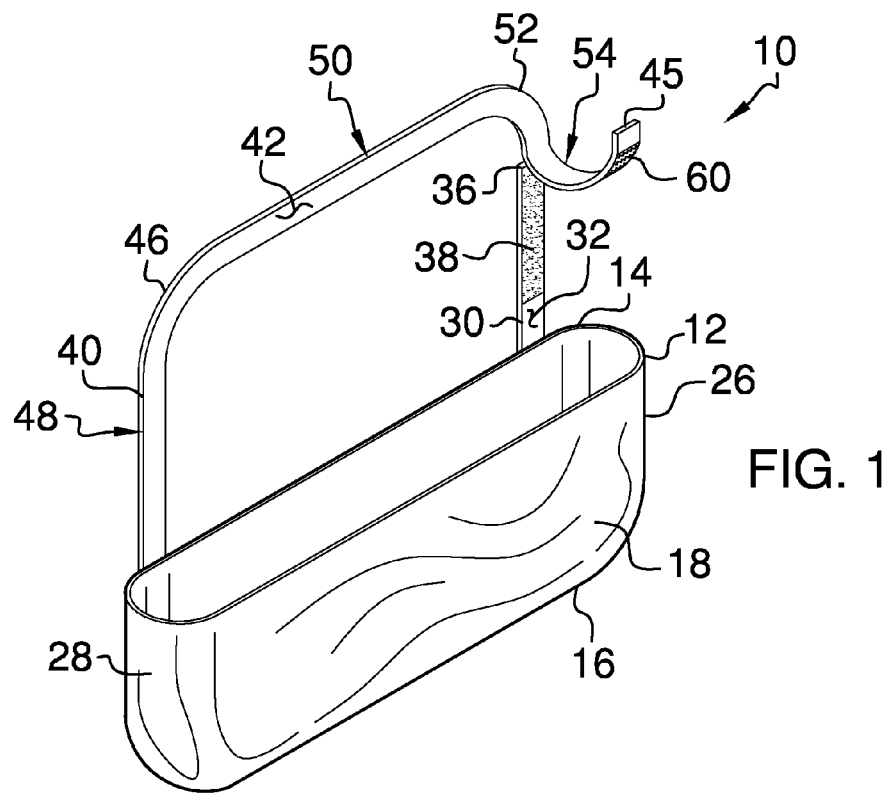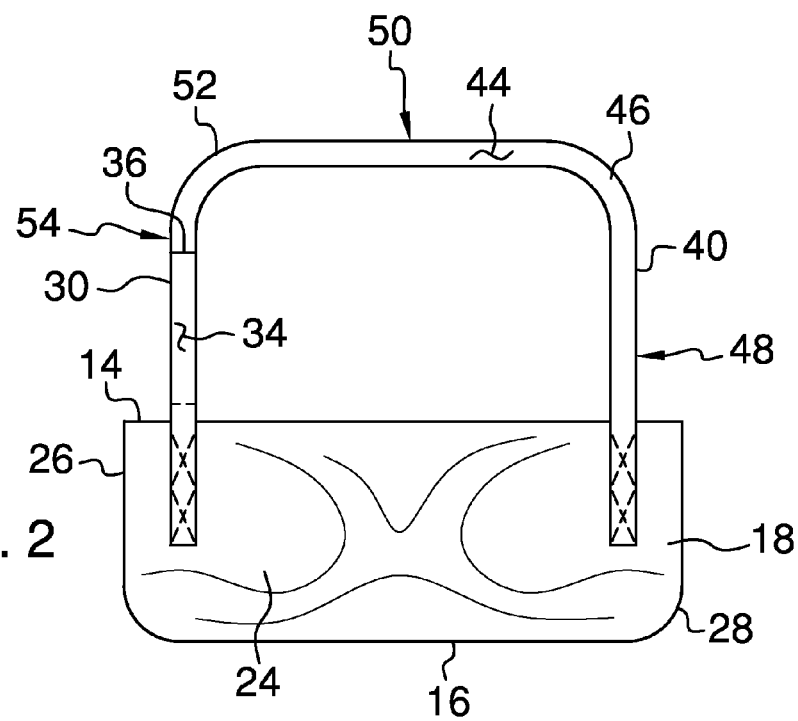

BODILY SUPPORT ASSEMBLY

BACKGROUND OF THE DISCLOSURE

Field of the Disclosure

The disclosure relates to support devices and more particularly pertains to a new support device for supporting a user's forearms while the user is seated.

SUMMARY OF THE DISCLOSURE

An embodiment of the disclosure meets the needs presented above by generally comprising a bag that may insertably receive each of pair of forearms of a user. A first strap is attached to the bag and a first coupler is attached to the first strap. A second strap is attached to the bag and the second strap may be extended around a neck of a user. A second coupler is attached to the second strap and the second coupler is complementary with respect to the first coupler. Thus, the first coupler and the second coupler retain the first strap and the second strap around the user's neck thereby facilitating the bag to support the user's forearms.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 1 is a front perspective view of a bodily support assembly according to an embodiment of the disclosure.

FIG. 2 is a back view of an embodiment of the disclosure.

DESCRIPTION OF THE PREFERRED EMBODIMENT

Figure 3:
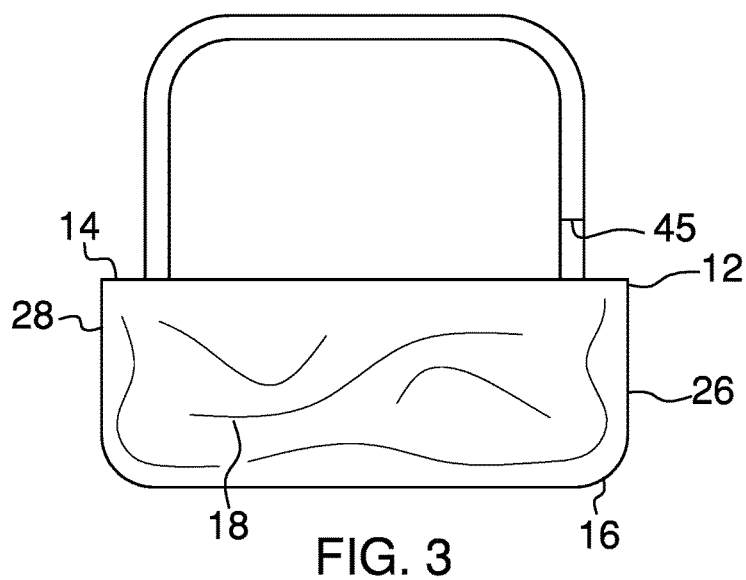
FIG. 3 is a front view of an embodiment of the disclosure.
Figure 4:
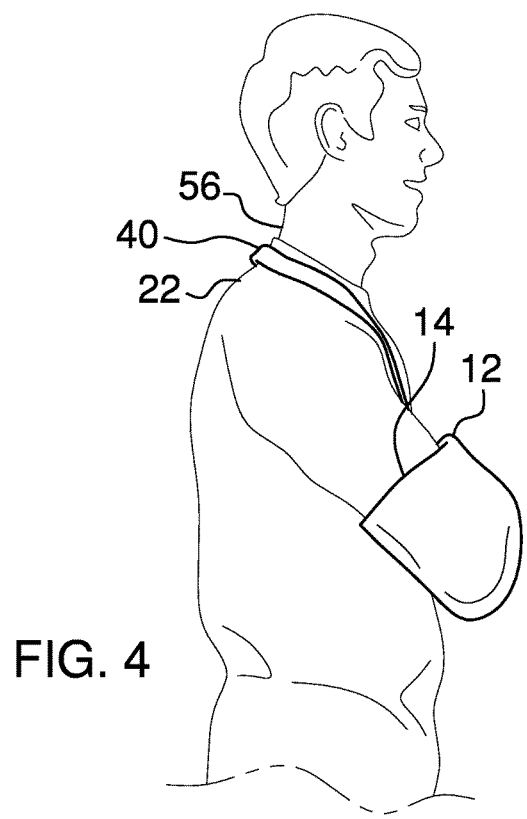
FIG. 4 is a right side in-use view of an embodiment of the disclosure.
Figure 5:
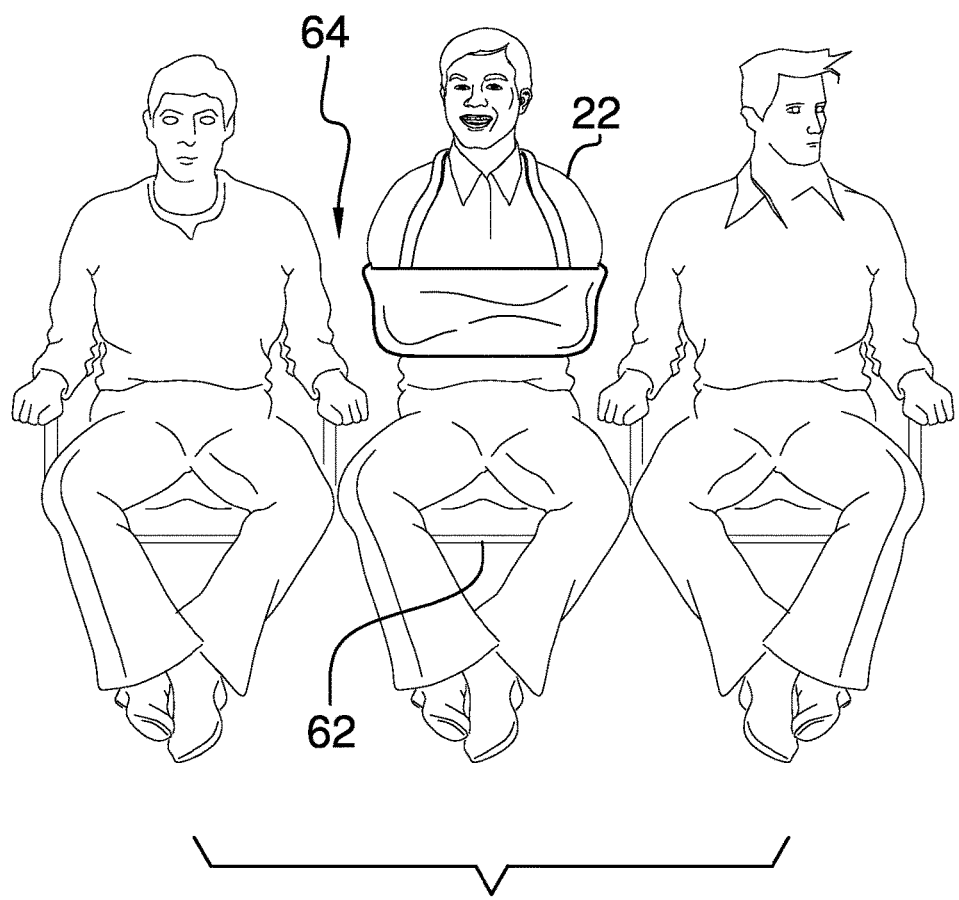
FIG. 5 is a perspective in-use view of an embodiment of the disclosure.

With reference now to the drawings, and in particular to FIGS. 1 through 5 thereof, a new support device embodying the principles and concepts of an embodiment of the disclosure and generally designated by the reference numeral 10 will be described.

As best illustrated in FIGS. 1 through 5, the bodily support assembly 10 generally comprises a bag 12 that has a top end 14, a bottom end 16 and a peripheral wall 18 extending between the top end 14 and the bottom end 16. The top end 14 is open and the bag 12 is substantially hollow. Thus, the bag 12 may insertably receive each of pair of forearms 20 of a user 22. The peripheral wall 18 has a back side 24, a first lateral side 26 and a second lateral side 28 and the bag 12 is elongated between the first lateral side 26 and the second lateral side 28.

A first strap 30 is provided that has a front surface 32 and a back surface 34. A portion of the front surface 32 is attached to the bag 12 having the first strap 30 extending upwardly from the top end 14. The first strap 30 has a distal end 36 with respect to the top end 14. The first strap 30 is positioned on the back side 24 and the first strap 30 is positioned adjacent to the first lateral side 26. A first coupler 38 is attached to the first strap 30 and the first coupler 38 is positioned on the front surface 32. The first coupler 38 extends substantially between the distal end 36 and the top end 14 of the bag 12.

A second strap 40 is provided that has a front surface 42 and a back surface 44. A portion of the front surface 42 of the second strap 40 is attached to the bag 12 having the second strap 40 extending upwardly from the top end 14. The second strap 40 has a distal end 45 with respect to the top end 14. The second strap 40 is positioned on the back side 24 and the second strap 40 is positioned adjacent to the second lateral side 28. The second strap 40 has a first bend 46 thereon and the first bend 46 is positioned closer to the top end 14 than the distal end 45 of the second strap 40. The first bend 46 defines a first portion 48 of the second strap 40 forming a right angle with respect to a second portion 50 of the second strap 40. The second portion 50 is spaced upwardly from and is coextensive with the top end 14.

The second strap 40 has a second bend 52 thereon that is positioned closer to the distal end 45 of the second strap 40 than the first bend 46. The second bend 52 defines a third portion 54 of the second strap 40 forms a right angle with respect to the second portion 50 and the third portion 54 extends downwardly toward the top end 14 of the bag 12. The second strap 40 has a U-shape thereby facilitating the second strap 40 to be extended around a neck 56 of the user 22 having the back side 24 of the bag 12 abutting a torso 58 of the user 22.

A second coupler 60 is attached to the second strap 40 and the second coupler 60 is positioned on the back surface 44 of the second strap 40. The second coupler 60 extends between the distal end 45 of the second strap 40 and the second bend 52. The second coupler 60 is complementary with respect to the first coupler 38 such that the first coupler 38 and the second coupler 60 retain the first strap 30 and the second strap 40 around the user's neck 56. Thus, the bag 12 may support the user's forearms 20 while the user 22 is seated. Each of the first coupler 38 and the second coupler 60 may comprise a hook and loop fastener.

In use, the user 22 sits on a seat 62. The seat 62 is located in a vehicle 64 utilized in the convention of public transportation. The vehicle 64 may be a bus, train, airplane or other vehicle that has multiple seats 62 positioned adjacent to one another. The second strap 40 is extended around the user's neck 56 and the first 38 and second 60 couplers are attached together. The user's forearms 20 are positioned within the bag 12 in order to support the user's forearms 20 while the user 22 is seated. The bag 12 allows the user 22 to avoid contact with other individuals while the user 22 is seated in public transportation and permits the user 22 to enjoy the comfort of having the user's forearms 20 being supported.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A bodily support assembly configured to support each of a user's arms, said assembly comprising:
   a bag being configured to insertably receive each of pair of forearms of a user, said bag having a top end, a bottom end and a peripheral wall extending between said top end and said bottom end, said top end being open, said peripheral wall having a back side, a first lateral side and a second lateral side, said bag being elongated between said first lateral side and said second lateral side;
   a first strap being attached to said bag, said first strap being positioned on said back side such that said first strap extends up from said open top;
   a first coupler being attached to said first strap;
   a second strap being attached to said bag, said second strap being positioned on said back side such that said second strap extends up from said open top, said second strap being configured to be extended around a neck of a user, said second strap has a first bend thereon, said first bend being positioned closer to said top end than said distal end of said second strap, said first bend defining a first portion of said second strap forming a right angle with respect to a second portion of said second strap, said second portion being spaced upwardly from and being coextensive with said top end, said second strap having a second bend thereon being positioned closer to said distal end of said second strap than said first bend, said second bend defining a third portion of said second strap forming a right angle with respect to said second portion, said third portion extending downwardly toward said top end of said bag, said second strap having a U-shape wherein said second strap is configured to be extended around a neck of a user having said back side of said bag abutting a torso of the user; and
   a second coupler being attached to said second strap, said second coupler being complementary with respect to said first coupler to couple said first coupler to said second coupler forming a single loop extended from said back side of said bag wherein said first coupler and said second coupler are configured to retain said first strap and said second strap around the user's neck with said top end of said bag being unobstructed by said first strap and said second strap thereby facilitating said bag to support the user's forearms, said second coupler being positioned on said back surface of said second strap, said second coupler extending between said distal end of said second strap and said second bend such that said first coupler and second coupler are each positioned proximate said open top wherein said first coupler and said second coupler are configured to be accessible to a hand on an arm positioned in said bag.

2. The assembly according to claim 1, wherein said first strap has a front surface and a back surface, a portion of said front surface being attached to said bag having said first strap extending upwardly from said top end, said first strap having a distal end with respect to said top end, said first strap being positioned adjacent to said first lateral side.

3. The assembly according to claim 2, further comprising said first coupler being positioned on said front surface, said first coupler extending between said distal end and said top end of said bag.

4. The assembly according to claim 1, wherein
   said second strap has a front surface and a back surface, a portion of said front surface of said second strap being attached to said bag having said second strap extending upwardly from said top end, said second strap having a distal end with respect to said top end, said second strap being positioned adjacent to said second lateral side.

5. A bodily support assembly configured to support each of a user's arms, said assembly comprising:
   a bag having a top end, a bottom end and a peripheral wall extending between said top end and said bottom end, said top end being open wherein said top end is configured to insertably receive each of pair of forearms of a user, said peripheral wall having a back side, a first lateral side and a second lateral side, said bag being elongated between said first lateral side and said second lateral side;
   a first strap having a front surface and a back surface, a portion of said front surface being attached to said bag having said first strap extending upwardly from said top end, said first strap having a distal end with respect to said top end, said first strap being positioned on said back side such that said first strap extends up from said open top, said first strap being positioned adjacent to said first lateral side;
   a first coupler being attached to said first strap, said first coupler being positioned on said front surface, said first coupler extending between said distal end and said top end of said bag;
   a second strap having a front surface and a back surface, a portion of said front surface of said second strap being attached to said bag having said second strap extending upwardly from said top end, said second strap having a distal end with respect to said top end, said second strap being positioned on said back side such that said second strap extends up from said open top, said second strap being positioned adjacent to said second lateral side, said second strap having a first bend thereon, said first bend being positioned closer to said top end than said distal end of said second strap, said first bend defining a first portion of said second strap forming a right angle with respect to a second portion of said second strap, said second portion being spaced upwardly from and being coextensive with said top end, said second strap having a second bend thereon being positioned closer to said distal end of said second strap than said first bend, said second bend defining a third portion of said second strap forming a right angle with respect to said second portion, said third portion extending downwardly toward said top end of said bag, said second strap having a U-shape wherein said second strap is configured to be extended around a neck of a user having said back side of said bag abutting a torso of the user; and a second coupler being attached to said second strap, said second coupler being positioned on said back surface of said second strap, said second coupler extending between said distal end of said second strap and said second bend such that said first coupler and second coupler are each positioned proximate said open top wherein said first coupler and said second coupler are configured to be accessible to a hand on an arm positioned in said bag, said second coupler being complementary with respect to said first coupler to couple said first coupler to said second coupler forming a single loop extending from said back side if said bag wherein said first coupler and said second coupler are configured to retain said first strap and said second strap around the user's neck with said top end of said bag being unobstructed by said first strap and said second strap thereby facilitating said bag to support the user's forearms.

\* \* \* \* \*